US012755847B2

(12) United States Patent
Wasilewicz et al.

(10) Patent No.: US 12,755,847 B2
(45) Date of Patent: Oct. 6, 2026

(54) METHOD FOR CREATING A PREDICTIVE MODEL FOR PREDICTING GLAUCOMA RISK IN A SUBJECT, METHOD FOR DETERMINING GLAUCOMA RISK IN A SUBJECT USING SUCH PREDICTIVE MODEL, DEVICE FOR PREDICTING GLAUCOMA RISK IN A SUBJECT, COMPUTER PROGRAM AND COMPUTER READABLE MEDIUM

(71) Applicants: INSTYTUT CHEMII BIOORGANICZNEJ PAN, Poznan (PL); Robert Henryk Wasilewicz, Poznan (PL)

(72) Inventors: Robert Henryk Wasilewicz, Poznan (PL); Cezary Mazurek, Poznan (PL); Juliusz Pukacki, Poznan (PL); Hubert Swierczynski, Poznan (PL)

(73) Assignees: Robert Wasilewicz, Poznan (PL); INSTYTUT CHEMII BIOORGANICZNEJ PAN, Poznan (PL)

( * ) Notice: Subject to any disclaimer, the term of this patent is extended or adjusted under 35 U.S.C. 154(b) by 29 days.

(21) Appl. No.: 17/206,376

(22) Filed: Mar. 19, 2021

(65) Prior Publication Data

US 2021/0319903 A1 Oct. 14, 2021

(30) Foreign Application Priority Data

Apr. 9, 2020 (EP) .................................... 20461527

(51) Int. Cl.
*G16H 50/30* (2018.01)
*A61B 3/16* (2006.01)
(Continued)

(52) U.S. Cl.
CPC ............... *G16H 50/30* (2018.01); *A61B 3/16* (2013.01); *A61B 5/0205* (2013.01); (Continued)

(58) Field of Classification Search
CPC ........ G16H 50/30; A61B 3/16; A61B 5/0205; A61B 5/7246; A61B 5/7264; A61B 5/7275
See application file for complete search history.

(56) References Cited

U.S. PATENT DOCUMENTS

2002/0005935 A1* 1/2002 Robin .................... A61B 5/411 351/224
2016/0100806 A1* 4/2016 Mwanza ............. A61B 5/7275 351/205

FOREIGN PATENT DOCUMENTS

WO WO-2020033736 A1 * 2/2020 ........... A61B 3/1241

OTHER PUBLICATIONS

Martin, Keith. 'Use of Machine Learning on Contact Lens Sensor-Derived Parameters for the Diagnosis of Primary Open-angle Glaucoma', American Journal of Ophthalmology Oct. 2018, vol. 194, pp. 46-53. Elsevier [online] (Year: 2018).*

(Continued)

*Primary Examiner* — Allen Porter
*Assistant Examiner* — Moussa Haddad
(74) *Attorney, Agent, or Firm* — Merchant & Gould P.C.

(57) ABSTRACT

The invention relates to a method (100) for creating a predictive model for predicting glaucoma risk in a subject, the method comprising: a step of creating a diagnostic model comprising, for each one of a plurality of subjects: recording (s101*a*) a 24-hour profile of eyeball parameters; dividing (s102*a*) the recorded 24-hour profile of eyeball parameters at least into subperiods: an initial subperiod (START—TP1); a (Continued)

subperiod preceding assuming a horizontal position for sleep (TP1—SLEEP); a subperiod following assuming a horizontal position for sleep (SLEEP—TP2); a subperiod preceding assuming a vertical position after sleep (TP2—WAKE); a subperiod following assuming a vertical position after sleep (WAKE—TP3) and a final subperiod (TP3—END); determining (s103*a*), in each subperiod, features describing a single subject in the form of at least one aggregating attribute; creating (s104) a record containing the determined features describing a single subject; assigning (s105) a label indicating a diagnosis (diseased/healthy) made by a physician to the created record. Furthermore, the method includes a step of creating a predictive model, based on a set of records created for the plurality of subjects, using supervised machine learning mechanisms based on one or more algorithms selected at least from regression algorithms, decision trees, Bayesian algorithms, ensemble algorithms and support vector-based algorithms.

Furthermore, the invention relates to a method for determining glaucoma risk in a subject, the method comprising creating, for a patient to be examined, a record containing the same feature set as the one created in the step (s104) of the method (100) for creating a predictive model and determining an allocation of the subject to a group of diseased or healthy subjects with determined probability using the predictive model created according to the method for creating a predictive model.

Furthermore, the invention relates to a device for predicting glaucoma in a subject, comprising means for performing methods according to the invention, and relates to a computer program comprising a program code for performing method steps according to the invention and to a computer readable medium on which the computer program is stored.

16 Claims, 6 Drawing Sheets

(51) Int. Cl.
*A61B 5/00* (2006.01)
*A61B 5/0205* (2006.01)
*G16H 50/20* (2018.01)

(52) U.S. Cl.
CPC .......... *A61B 5/7246* (2013.01); *A61B 5/7264* (2013.01); *A61B 5/7275* (2013.01); *G16H 50/20* (2018.01)

(56) References Cited

OTHER PUBLICATIONS

Ho, Chun. 'Role of 24-Hour Intraocular Pressure Monitoring in Glaucoma Management', Journal of Ophthalmology Sep. 2019, pp. 1-13. https://doi.org/10.1155/2019/3632197 (Year: 2019).*

Grisler, Christophe. 'Towards Glaucoma Detection Using Intraocular Pressure Monitoring', International Conference of Soft Computing and Pattern Recognition, IEEE, Aug. 2014, pp. 255-260. https://doi.org/10.1155/2019/3632197 (Year: 2014).*

Leeman et al. ("Glaucoma and Blood Pressure", Hypertension, vol. 73, Issue 5, May 2019; pp. 944-950 https://doi.org/10.1161/HYPERTENSIONAHA.118.11507) (Year: 2019).*

Hara et al. ("Increase of Peak Intraocular Pressure During Sleep in Reproduced Diurnal Changes by Posture" Arch Ophthalmol. 2006; 124(2):165-168. doi:10.1001/archopht.124.2.165) (Year: 2006).*

Quaranta et al. ("Untreated 24-h intraocular pressures measured with Goldmann applanation tonometry vs nighttime supine pressures with Perkins applanation tonometry" Eye (2010) 24, 1252-1258, 2009) (Year: 2009).*

Martin, Kieth R. et al. Use of machine learning on contact lens sensor-derived parameters for the diagnosis of primary open-angle glaucoma. American Journal of Ophthalmology. vol 194. Oct. 2018.

Gisler, Christphe et al. Towards glaucoma detection using intraocular pressure monitoring. 2014 6$^{th}$ International conference of soft computing and pattern recognition. Aug. 11, 2012, pp. 255-260.

Wasilewicz, Robert Henryk et al. Daily biorhythms of ocular volume changes and the cardiovascular system functional parameters in healthy, ocular hypertension, normal tension and primary open angle glaucoma populations. ARVO Annual Meeting Abstract, Apr. 1, 2014.

Wasilewicz et al. 24 hour continuous ocular tonography Triggerfish and biorhythms of the cardiovascular system functional parameters in healthy and glaucoma populations. Acta Ophthalmologica, Wiley Online Library, Aug. 6, 2013.

Susanna, Carolina N. et al. A Prospective Longitudinal Study to Investigate Corneal Hysteresis as a Risk Factor for Predicting Development of Glaucoma. American Journal of Ophthalmology, vol. 187, Mar. 1, 2018, pp. 148-152.

Doozandeh, Azadeh et al. Corneal profile in primary congenital glaucoma. Acta Ophthalmologica: the Ophthalmological Journal of the Nordic Countries, vol. 95, No. 7, Jan. 31, 2017, pp. e575-e581.

European Search Report issued for EP20461527.2, completed Sep. 7, 2020.

* cited by examiner

METHOD FOR CREATING A PREDICTIVE MODEL FOR PREDICTING GLAUCOMA RISK IN A SUBJECT, METHOD FOR DETERMINING GLAUCOMA RISK IN A SUBJECT USING SUCH PREDICTIVE MODEL, DEVICE FOR PREDICTING GLAUCOMA RISK IN A SUBJECT, COMPUTER PROGRAM AND COMPUTER READABLE MEDIUM

CROSS-REFERENCE TO RELATED APPLICATIONS

This application claims priority under 35 U.S.C. § 119 to European Patent Application No. 20461527.2, filed Apr. 9, 2020, the disclosures of which is expressly incorporated by reference herein.

FIELD

The present invention relates to a method for creating a predictive model for predicting glaucoma risk in a subject, a method for determining glaucoma risk in a subject using such predictive model, a device for predicting glaucoma risk in a subject for performing said methods, a computer program and a computer readable medium. In particular, the invention relates to creating and using the predictive model for predicting glaucoma in a subject which is based on specific features determined from an eyeball biorhythm, using artificial intelligence and machine learning methods.

BACKGROUND OF THE INVENTION

Glaucoma is a progressive optic neuropathy which is the most common cause of irreversible vision loss in the world. Its pathomechanism is associated with a change in lamina cribrosa phenotype under the influence of excessive mechanical forces, which leads to neurotrophic deprivation and subsequent accelerated process of retinal ganglion cell apoptosis. Loss of retinal ganglion cells leads to disruption of the functional visual pathway continuity which leads to the development of specific, depending on the architecture of the retina and optic nerve defects in the visual field. Those defects appear clinically when at least 30 to 50% of the ganglion cells of a given area of the retina is lost.

Elevated intraocular pressure is the most important known risk factor for the development of glaucomatous optic neuropathy (specificity 0.85/sensitivity 0.3/AUC 0.6), and its reduction is the only clinically proven way to reduce the risk of its progression. Modern practice in the field of glaucoma diagnosis or its risk assessment which is based mainly or exclusively on the assessment of intraocular pressure elevation in extreme cases may result in erroneous diagnosis and serious consequences for the subject, especially in cases of glaucoma presence despite of normal intraocular pressure. Furthermore, elevated intraocular pressure may have various grounds which further impairs a correct diagnosis. In order to provide a more effective diagnosis, in addition to the intraocular pressure test, other methods may also be used to assess the risk of glaucoma, such as, for example, fundus examination, visual field examination or optical tomography. However, performing a number of tests is uncomfortable for the subject, time-consuming, and the final assessment of the subject's health state requires many factors to be taken into consideration, and therefore is complicated and prone to errors.

In view of the above, there is a need in the prior art to develop a more effective and reliable method for determining glaucoma risk that will allow to simplify the subject examination process and will provide a quick and reliable diagnosis.

Therefore, it is the object of the present invention to provide a suitable method and a device for predicting glaucoma risk in a subject which at least mitigate the above-mentioned one or more problems in the prior art.

Document Wasilewicz R H, Wasilewicz P K, Mazurek C, et al. "Daily biorhythms of ocular volume changes and the cardiovascular system functional parameters in healthy, ocular hypertension, normal tension and primary open angle glaucoma populations", ARVO Annual Meeting Abstract, April 2014, describes relationships between eyeball biorhythm parameters and cardiovascular system parameters in individual ranges of the 24-hour period.

The starting point for the development of the present invention was the development of a method for determining characteristic features in the eyeball biorhythm parameters by the inventors, which features proved to be helpful in predicting glaucoma. Determined features enabled a predictive model to be created which on the basis of the above-mentioned features determined for a sufficiently large group of examined and diagnosed subjects is able to classify an examined subject as healthy/diseased with determined probability based on an analogous feature set. Such indication based on previous diagnoses for subjects for which identical features have been determined may be very helpful for the initial assessment of glaucoma risk and can assist physicians in making a diagnosis and proposing a better treatment method. Furthermore, the developed method may be based on an extended feature set including, among others, eyeball parameter and cardiovascular system parameter correlations, subject's age, corneal resistance factor and corneal hysteresis.

SUMMARY OF INVENTION

According to the invention a method for creating a predictive model for predicting glaucoma risk in a subject according to claim 1, a method for determining glaucoma risk in a subject using the predictive model according to claim 11, a device for predicting glaucoma risk in a subject according to claim 12, and a computer program and a computer readable medium according to claims 14 and 15 respectively are provided.

The method for creating a predictive model for predicting glaucoma risk in a subject according to the invention includes a step of creating a diagnostic model comprising, for each one of a plurality of subjects:

a) recording a 24-hour profile of eyeball parameters;
b) dividing the recorded 24-hour profile of eyeball parameters at least into subperiods: an initial subperiod; a subperiod preceding assuming a horizontal position for sleep; a subperiod following assuming a horizontal position for sleep; a subperiod preceding assuming a vertical position after sleep; a subperiod following assuming a vertical position after sleep; a final subperiod;
c) determining, in each subperiod, features describing a single subject in the form of at least one aggregating attribute;
d) creating a record containing the determined features describing a single subject;
e) assigning a label indicating a diagnosis (diseased/healthy) made by a physician to the created record.

Furthermore, said method according to the invention includes a step of creating a predictive model, based on a set of records created for the plurality of subjects, using supervised machine learning mechanisms based on one or more algorithms selected at least from regression algorithms, decision trees, Bayesian algorithms, ensemble algorithms and support vector-based algorithms.

In a preferred embodiment of the method, the predictive model is created using 10-fold cross-validation.

In another preferred embodiment of the method, the aggregating attributes are selected from a group including: a sum of the area under the curve in a subperiod, the slope angle of a linear regression line in a subperiod, the total variation in a subperiod, representative values of the discrete Fourier transform in a subperiod.

In yet another preferred embodiment of the method, the eyeball parameters are selected from a group including: the circumference at the corneoscleral limbus of an eyeball and intraocular pressure.

In yet another preferred embodiment of the method, simultaneously with recording the 24-hour profile of eyeball parameters cardiovascular system parameters are recorded, in the determined subperiods correlations between the eyeball parameters and the cardiovascular system parameters are calculated, and to the record describing a single subject created in the step of creating a record the calculated correlation parameters are appended as further features.

In yet another preferred embodiment of the method, the cardiovascular system parameters are selected from a group including: blood pressure (BP): systolic arterial pressure (SAP), diastolic arterial pressure (DAP), mean arterial pressure (MAP), heart rate (HR), oxygen blood saturation ($SpO_2$) and cardiac output fraction calculated according to the formula: CO=[(SAP−DAP)/SAP+DAP)]×HR.

In yet another preferred embodiment of the method, one or more additional features selected from a group including: subject's age, corneal resistance factor and corneal hysteresis are determined and appended to the record describing a single subject created in the step of creating a record.

In yet another preferred embodiment of the method, the record describing a single subject is limited to a selected subset of the all determined features.

In yet another preferred embodiment of the method, the determined subperiods furthermore include a subperiod from the session start to assuming a horizontal position for sleep and/or a subperiod from assuming a horizontal position for sleep to assuming a vertical position after sleep and/or a subperiod from assuming a horizontal position at 14:00 to assuming a vertical position at 15:30 with sustained consciousness.

In yet another preferred embodiment of the method, the boundaries defining particular subperiods are as follows: 5 hours before assuming a horizontal position for sleep, assuming a horizontal position for sleep+2 hours, assuming a vertical position after sleep+2 hours.

A method for determining glaucoma risk in a subject according to the invention includes: creating, for a patient to be examined, a record containing the same feature set as the one created in the step of creating a record of the method for creating a predictive model, and determining an allocation of the subject to a group of diseased or healthy subjects with determined probability using the predictive model created according to the method for creating a predictive model disclosed above.

A device for predicting glaucoma in a subject according to the invention comprises means for recording eyeball parameters; means for recording cardiovascular system parameters; a control circuit having a communication connection with the means; a processor installed in the control circuit; a memory installed in the control circuit and operatively coupled to the processor; an output device for presenting results having a communication connection with the control circuit. Furthermore, the processor is configured to execute a program code stored in the memory for performing the steps of the methods disclosed above.

In a preferred embodiment of the device, the means for recording eyeball parameters, the means for recording cardiovascular system parameters and/or the output device are arranged in a remote location with respect to the control circuit, and the communication connections are communication network connections.

The invention also relates to a computer program comprising a program code for performing method steps according to the invention and to a computer readable medium on which the computer program is stored.

The solutions provided according to the invention find application in an intelligent physician decision support system which enables an ultra-early risk assessment of glaucoma neuropathy and the description of its factors in the population of people observed for glaucoma, subjects with a positive family history and ocular hypertension. As a result it is possible to personalize the methods of local and systemic therapy in glaucomatous subjects with an indication of individual risk factors for disease progression.

Further features and advantages of the present invention will become apparent after reading the description presented below in connection with the attached drawing, in which FIG. 1 shows a schematic block diagram illustrating successive steps of a method for creating a predictive model according to the invention.

DETAILED DESCRIPTION OF EMBODIMENTS OF THE INVENTION

Preferred embodiments are described below. Details of particular embodiments of the method apply at the same time, in the relevant scope, to embodiments of the device. Therefore, the repeated description will be omitted.

The subject solution is mainly based on the processing and analysis of data from daily eyeball biorhythm measurements and, optionally, from daily cardiovascular system parameter measurements. Additionally, permanent patient characteristics such as age, corneal resistance factor or corneal hysteresis can be used as a variant, which will be described in more detail below.

In order to perform the analytical process, it is necessary to construct a predictive model that will be used to determine a predicted health state of a subject along with probability of assessment accuracy. In practice, this will be an indication for the physician that a person classified as diseased has parameters similar to those of people diagnosed with the disease. It will not necessarily be an indication that the disease has already occurred.

In order to perform an analysis for a given subject, it is necessary to provide raw data from eyeball biorhythm monitoring devices and, optionally, changes in cardiovascular parameters over a 24-hour profile. The presented embodiment is based on data from specific devices described below.

Figure 1:
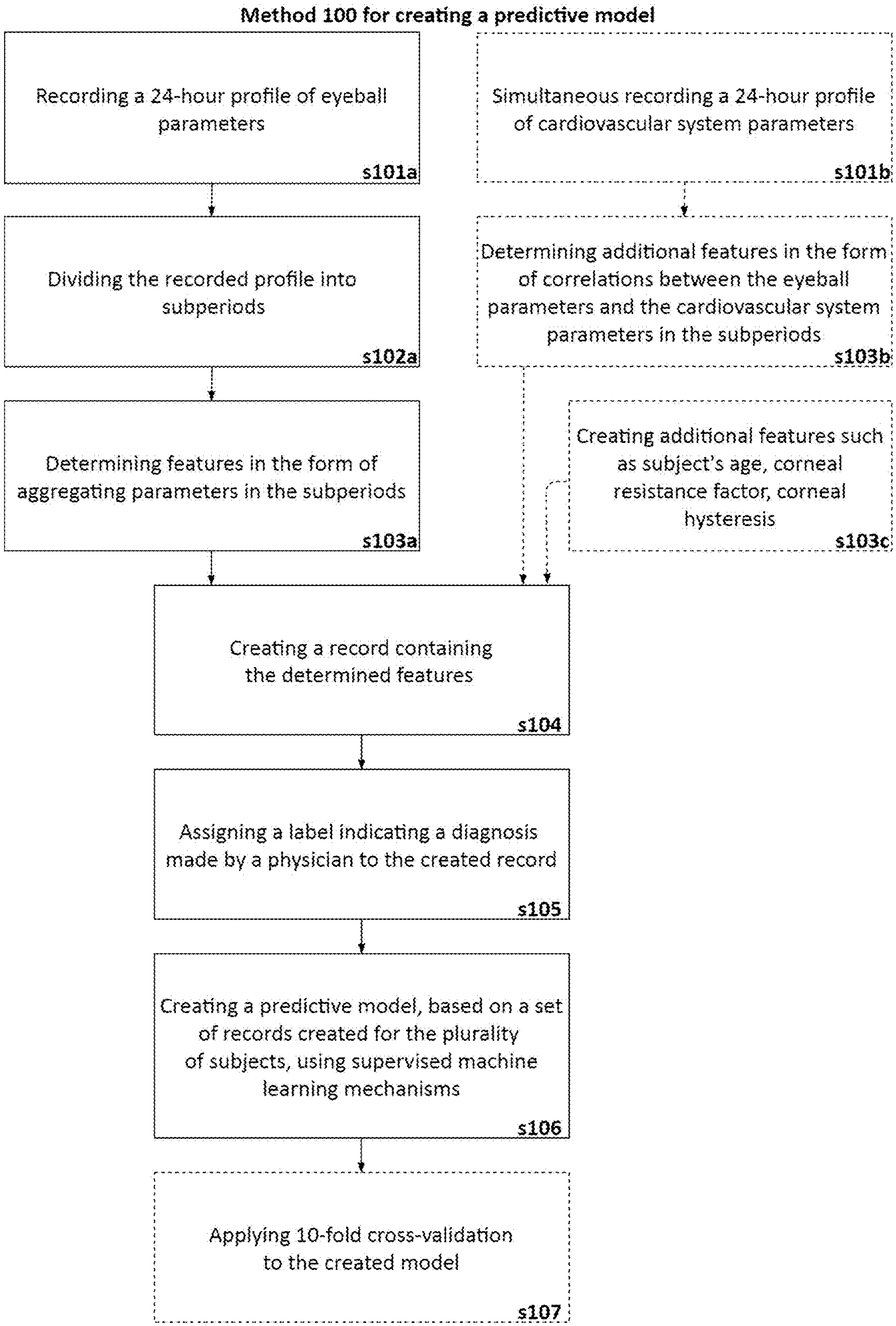

FIG. 1 shows a schematic block diagram illustrating successive steps of the method 100 for creating a predictive model for determining predicted health state of a subject. Blocks and arrows describing the relationships between blocks in FIG. 1 shown using dashed lines present a preferred addition to the described method 100, but are not necessary for its functioning.

In order to create a predictive model it is necessary to gather a sufficiently large set of data describing a diverse group of subjects. Successive steps s101*a*, s102*a*, s103*a*, s104 and s105 of the method 100 described below, similarly as optional steps s101*b*, s103*b* and s103*c*, are therefore analogously performed for each one of a plurality of subjects in order to provide so-called training data.

In step s101*a* a 24-hour profile of eyeball parameters is recoded. At this point it is noted that as eyeball parameters all parameters should be understood which describe features of an eyeball, such as, e.g., the circumference at the corneoscleral limbus of an eyeball, intraocular pressure (IOP) and similar parameters describing the variation of an eyeball biorhythm but these are only non-limiting examples. The person skilled in the art will notice other relevant eyeball parameters that are not specifically mentioned here. All the parameters listed above are values which are variable both individually and as a function of time. Data sequences resulting from the registration of the above parameters as a function of time for the 24-hour period are also referred to as the biorhythms in the present disclosure.

In optional step s101*b*, simultaneously with step s101*a*, a 24-hour profile of cardiovascular system parameters is recorded. At this point it is noted that as cardiovascular system parameters all parameters should be understood which describe cardiovascular system, such as, e.g., blood pressure (BP): systolic arterial pressure (SAP), diastolic arterial pressure (DAP), mean arterial pressure (MAP), heart rate (HR), oxygen blood saturation (SpO2) and cardiac output fraction calculated according to the formula: CO=[(SAP−DAP)/SAP+DAP)]×HR, but these are only non-limiting examples. The person skilled in the art will notice other relevant cardiovascular system parameters that are not specifically mentioned here. All the parameters listed above are values which are variable both individually and as a function of time. Data sequences resulting from the registration of the above parameters as a function of time for the 24-hour period are also referred to as the biorhythms in the present disclosure.

For the recording of the above-mentioned biorhythms, any commercially available systems can be used, such as e.g. TRIGGERFISH®, PMCL, SOMNOTOUCH NIBP® systems and the like, however the invention is not limited to them and any other devices and systems developed in the future and/or having a similar function can be used as long as they can provide the needed data sequences, both at intervals and in continuous mode.

Figure 2:
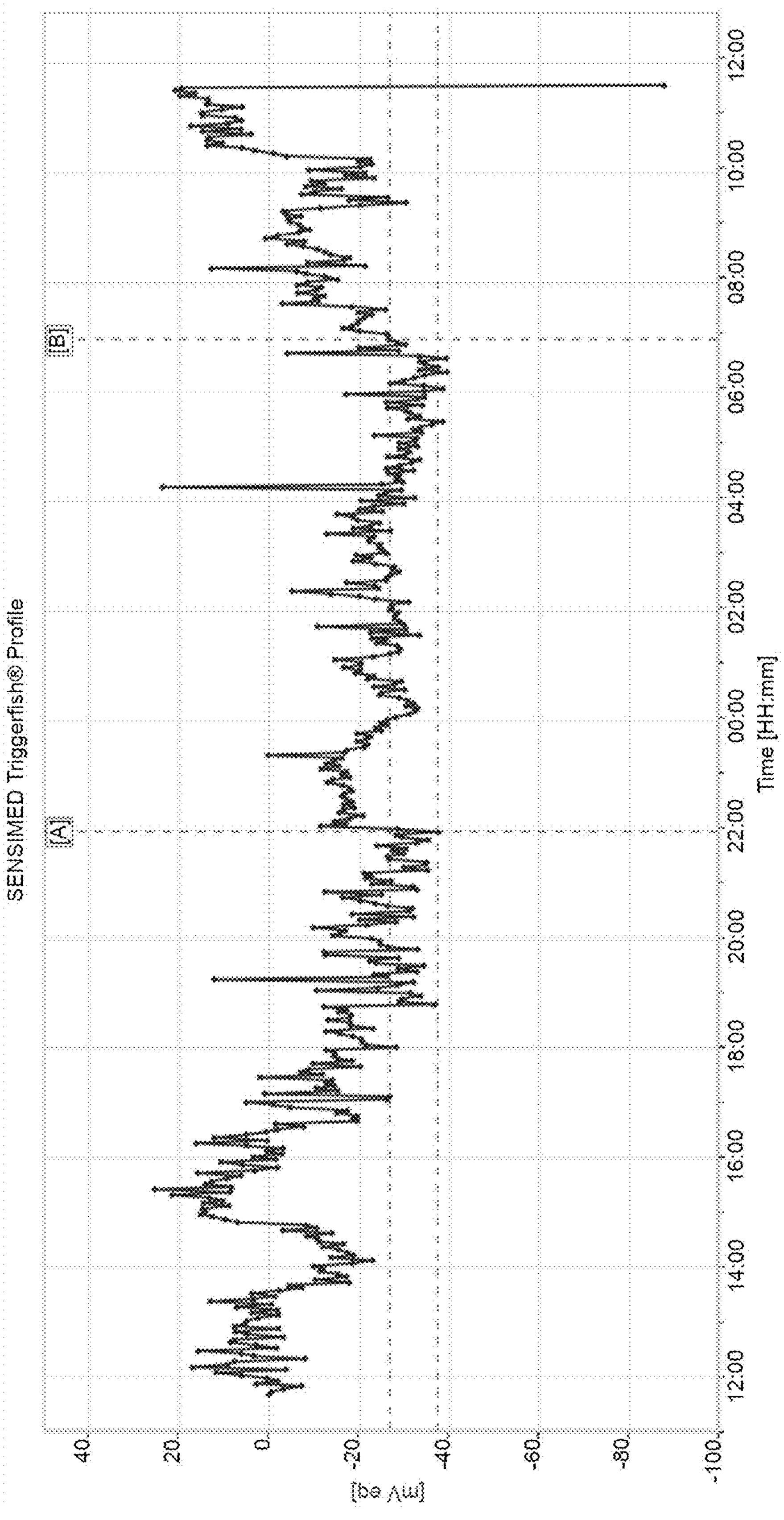
FIG. 2 shows an exemplary 24-hour variation profile of an eyeball circumference at the corneoscleral limbus.
Figure 3:
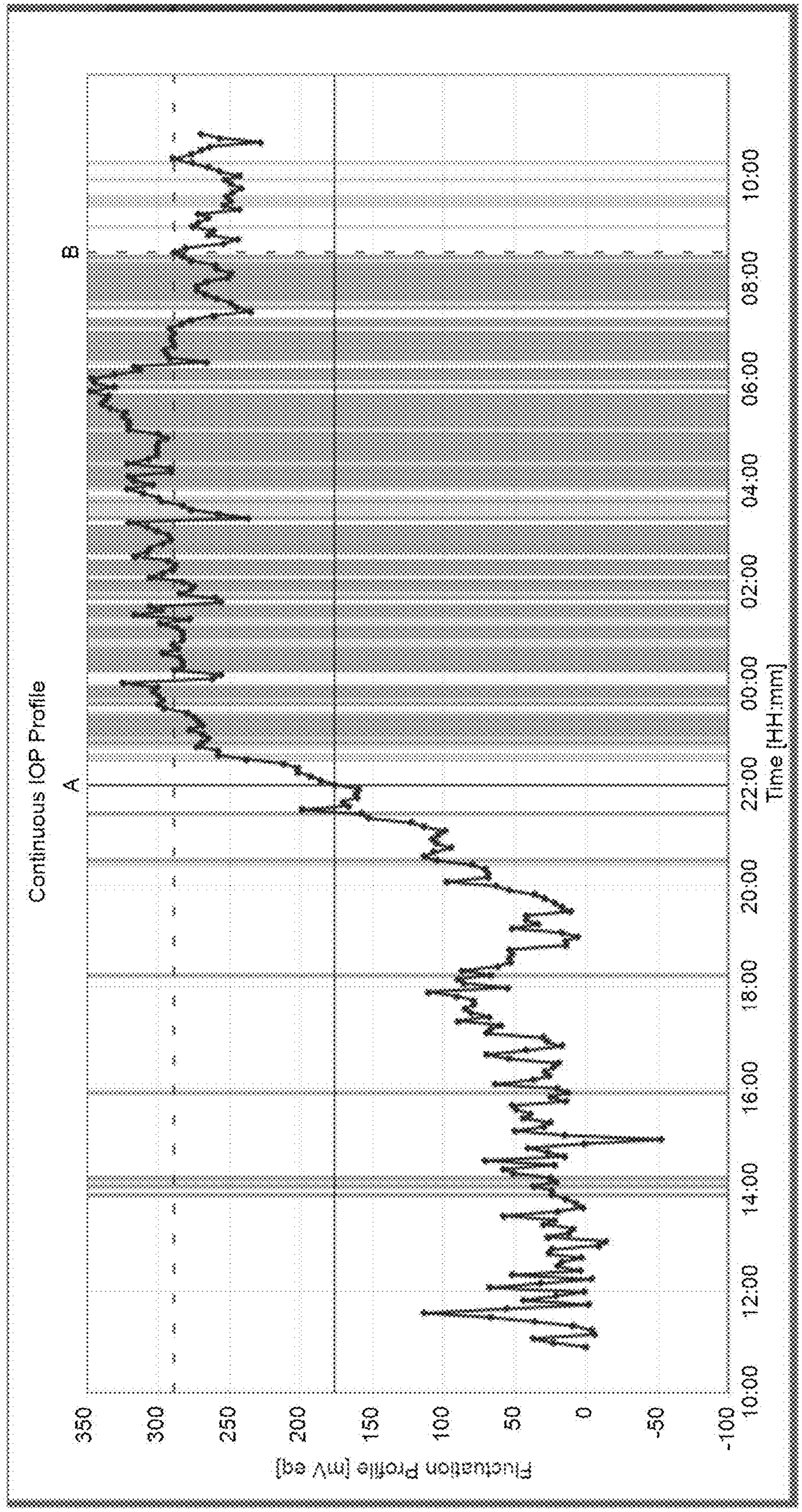
FIG. 3 shows an exemplary 24-hour variation profile of intraocular pressure.
Figure 4:
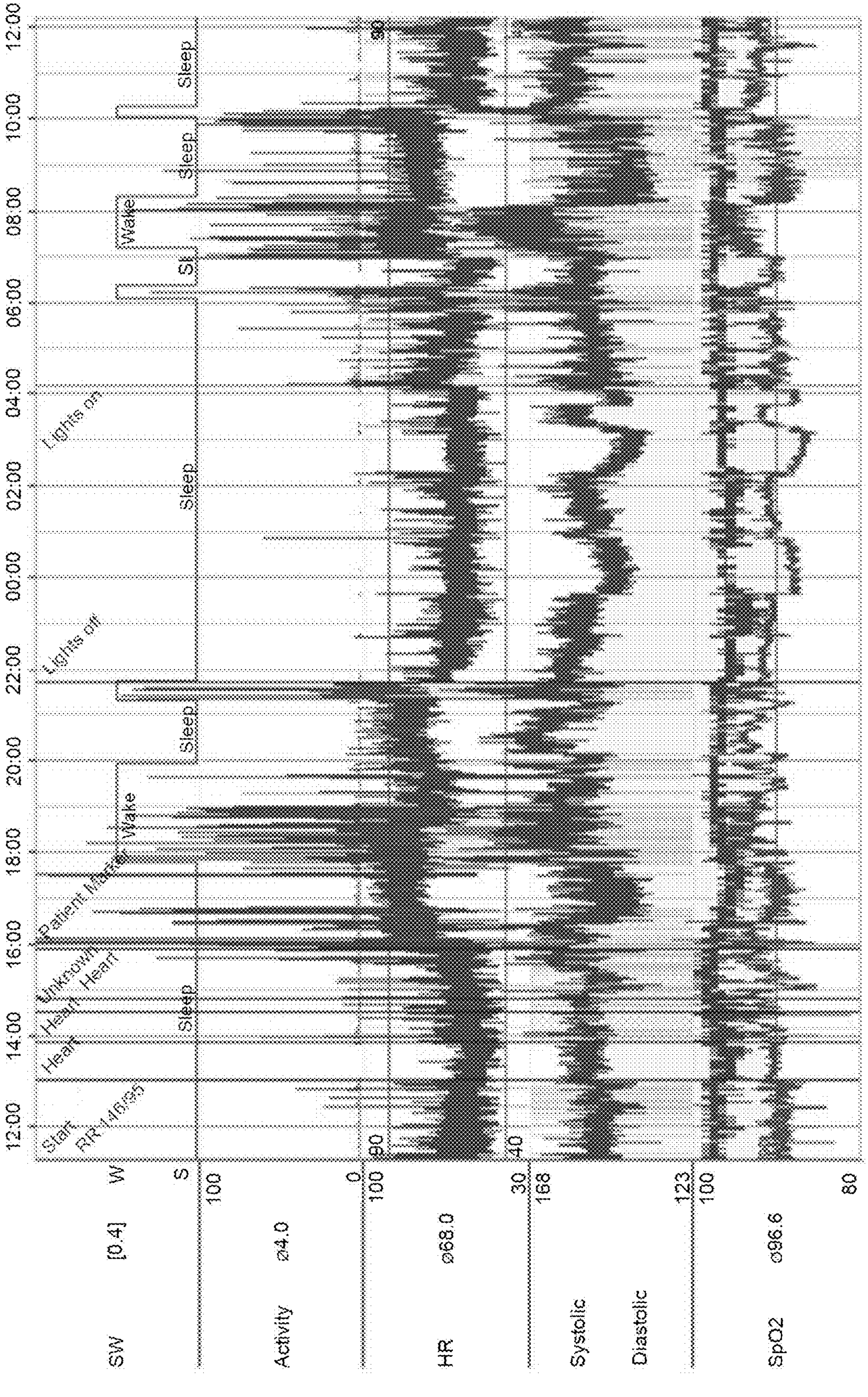
FIG. 4 shows an exemplary 24-hour variation profile of functional cardiovascular system parameters.

FIGS. 2-4 show exemplary diagrams of selected parameters as a function of time that can be used in the present invention and can be helpful for understanding the principles of the present invention.

FIG. 2 shows an exemplary 24-hour variation profile of the circumference at the corneoscleral limbus of an eyeball obtained by means of the TRIGGERFISH® system (Sensimed AG, Switzerland) which may be used in the present invention. In this system, data is recorded with a frequency of 10 Hz every 5 minutes in a 30-second measurement window. The data unit is mV. The median value of the data sequence from a given measurement window creates a point on the 24-hour timeline. Recording a set of these points at 5-minute intervals creates a time curve describing an individual biorhythm of circumferential dimensional changes at the corneoscleral limbus of an eyeball.

FIG. 3 shows an exemplary 24-hour variation profile of intraocular pressure (IOP) obtained by means of the PMCL system (Sensimed AG, Switzerland) which may be used in the present invention. In this case, the data recording is continuous with division into 180-second measurement windows in which data is recorded within two subperiods; at a frequency of 50 Hz for the first 30 seconds and at a frequency of 1 Hz during the remaining 150 seconds of the measurement window. The data unit is mmHg. The median value of the data sequence from a given measurement window creates a point on the 24-hour timeline. A record of a set of these points at 3-minute intervals creates a time curve describing an individual biorhythm of intraocular pressure variations.

FIG. 4 shows an exemplary 24-hour variation profile of functional cardiovascular system parameters obtained by means of the SOMNOTOUCH NIBP® system (Somnomedics AG, Germany). This system enables obtaining a 24-hour variation profile of functional cardiovascular system parameters in a continuous mode (beat-to-beat) using the PTT (pulse-transit-time) method. The functional parameters described are: systolic arterial pressure (SAP), diastolic arterial pressure (DAP), mean arterial pressure (MAP), heart rate (HR) and oxygen blood saturation (SpO2) and additionally cardiac output (CO) fraction calculated according to the formula: CO=[(SAP−DAP)/SAP+DAP]×HR. Data units are, respectively: mmHg, number of heart beats per minute, %.

Returning to FIG. 1, the data sequences for the parameters obtained in steps s101*a* and s101*b* are then subjected to a pre-processing to give them the desired form adapted for further processing. In the case of simultaneous recording eyeball parameters and cardiovascular system parameters, it may be necessary to synchronize the recorded data and to provide a compatible form for both sequences. This is especially important in case of data originating from different systems, i.e. recorded in different modes (e.g. continuous/discrete) and/or recorded in a different way e.g. at different frequencies or at different time points. As a result, sets of parameters that correspond to each other in time are obtained on one timeline, which parameters describe the biorhythm of the eyeball on one side and the cardiovascular system on the other. Such arrangement of data enables, among others, correlation calculation for data from both profiles at defined time points, which correlation is to be used in the later stages. In the presented embodiment, the recorded data is subjected to preliminary processing in such a way that parameter values are obtained at time points being full minutes, so that the correlated parameters are the median values of parameters read from devices in a given minute. However, the invention is not limited to this embodiment and any suitable time points can be selected, e.g. with a 30-second, 2-minute, 5-minute increment, etc. Any known techniques may be used to determine individual parameter values at the required time points that take into account adjacent and/or near values, e.g. median calculation, approximation, interpolation, etc.

Figure 5:
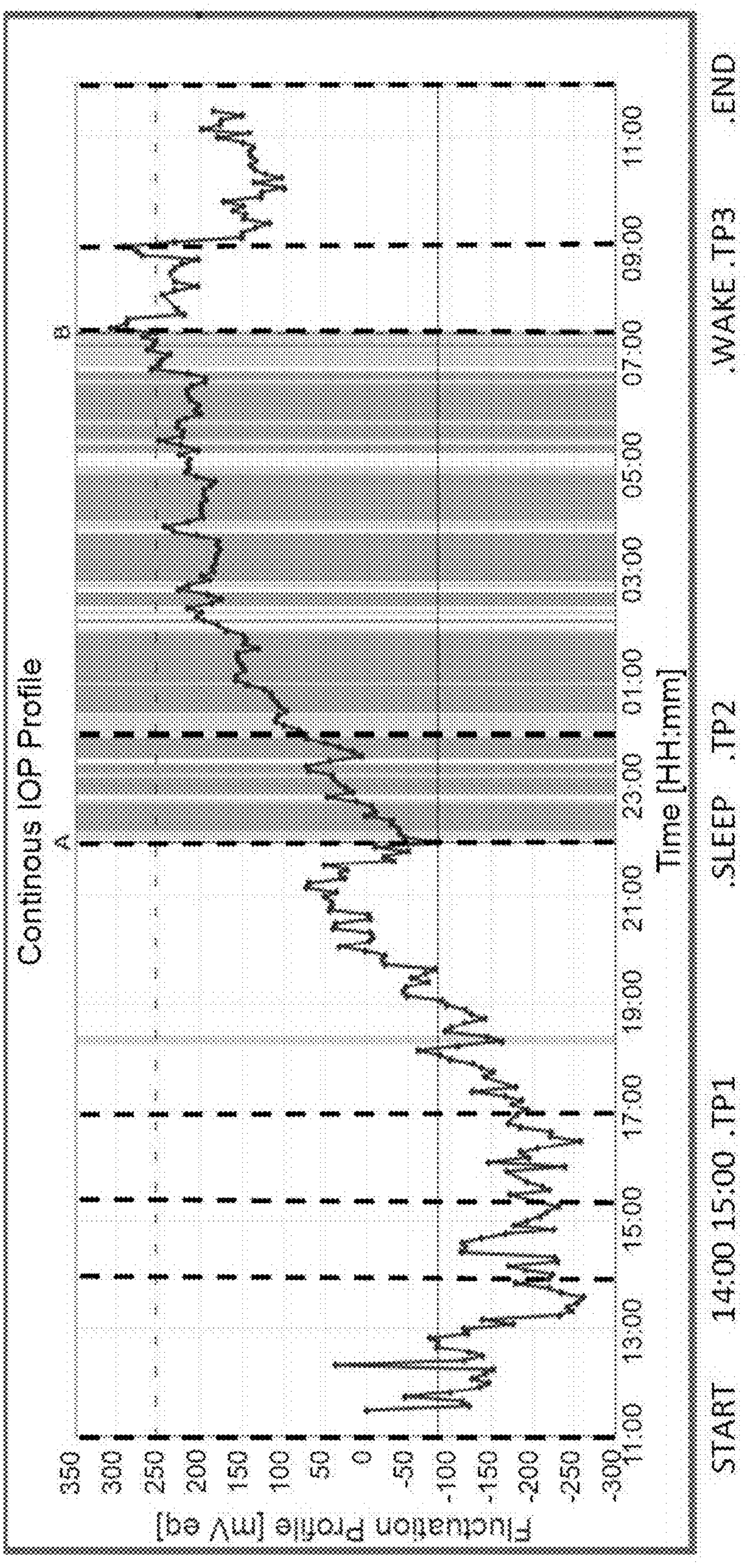
FIG. 5 shows an exemplary 24-hour variation profile of intraocular pressure divided into subperiods.

In step s102$a$, the pre-processed eyeball parameters are allocated to characteristic subperiods where it will be possible to determine the features used to construct the predictive model. In the case where cardiovascular system parameters in the step s101$b$ are also recorded, both synchronized profiles from steps s101$a$ and s101$b$ are divided into said identical subperiods. FIG. 5 shows an exemplary division into subperiods for a 24-hour description of variability of intraocular pressure (IOP), wherein identical division also occurs in an analogous way for the cardiovascular system parameters (not shown).

In the presented embodiment, 9 original subperiods of comparative data analysis were determined based on the comparative analysis of biorhythms of circumferential dimensional changes at the corneoscleral limbus of an eyeball, intraocular pressure and ocular pulse amplitude, and the corresponding specificity of human behaviour associated with circadian rhythm. The individual subperiods defined by particular boundary time points START, TP1, SLEEP, TP2, WAKE, TP3, END are briefly characterized below:

From "session start" to "5 hours before assuming a horizontal position for sleep": START—TP1

This subperiod describes relationships between the systems during daily activity (vertical position) of a given person in time when specific volume/IOP change patterns of the eyeball occur, caused mainly by cardiovascular system parameters variability resulting from individual behaviour types specific for a given person.

From "5 hours before assuming a horizontal position for sleep" to "assuming a horizontal position for sleep": TP1—SLEEP This subperiod describes relationships between the systems during daily activity of a given person (vertical position), in time when specific changes in the human endocrine system occur that influence the eyeball volume/IOP and cardiovascular system From "assuming a horizontal position for sleep" to "assuming a horizontal position for sleep+2 hours": SLEEP—TP2

This subperiod describes relationships between the systems during the first hours of sleep (horizontal position) of a given person in time when dynamic continuous volume/IOP changes of the eyeball and changes in cardiovascular system parameters occur resulting from the change in body position from vertical to horizontal, sleep and accompanying changes in the human endocrine system.

From "assuming a horizontal position for sleep+2 hours" to "assuming a vertical position after sleep": TP2—WAKE This subperiod describes relationships between the systems during sleep (horizontal position) of a given person in which time the eyeball volume/IOP change patterns are associated with fixed horizontal body position and associated with it changes in cardiovascular system parameters, blood saturation disorders, and sleep apnea.

From "assuming a vertical position after sleep" to "assuming a vertical position after sleep+2 hours": WAKE—TP3

This subperiod describes relationships between the systems during the first hours of daily activity (vertical position) of a given person in time when there are dynamic continuous changes in the eyeball volume and cardiovascular system parameters, resulting from the change in body position from horizontal to vertical, from changes in the human endocrine system and from pathognomonic behaviour of episcleral vessels of the eyeball resulting from their interaction with the sensor of the eyeball volume/IOP change assessment systems in the form of contact lens.

From "assuming a vertical position after sleep+2 hours" to the session end: TP3—END This subperiod describes relationships between the systems during daily activity (vertical position) of a given person in time when specific volume/IOP change patterns of the eyeball occur, caused mainly by the cardiovascular system parameters variability resulting from individual behaviour types specific for a given person.

From "session start" to "assuming a horizontal position for sleep": START-SLEEP

This subperiod describes relationships between the systems during daily activity of a given person.

From "assuming a horizontal position for sleep" to "assuming a vertical position after sleep": SLEEP—WAKE This subperiod describes relationships between the systems during sleep of a given person.

From "assuming a horizontal position at 14:00" to "assuming a vertical position at 15:30" with sustained consciousness (lying without sleep): TIME 14:00-TIME 15:30

This subperiod describes relationships between the systems during daily activity of a given person after assuming a horizontal position-functional test.

Although in the presented embodiment 9 subperiods are used which turned out to be beneficial for the implementation of the invention, the skilled person in the art will notice that the presented division is only exemplary and more or less subperiods can be used, and other time points can be selected in a 24-hour profile which will define the boundaries of particular subperiods that are specific for given patient conditions, without departing from the scope of the invention.

In step s103$a$, for each one of a plurality of subjects, based on the processed data of the eyeball parameter profile and within the determined subperiods, features in the form of aggregation parameters are determined which are used to create a diagnostic model. As mentioned earlier, for this purpose a sufficiently large set of data describing a diverse group of subjects should be gathered and used.

The process of determining (extracting) features consists in determining a limited set of features that can be used to construct a diagnostic model using machine learning methods. This is related to the specificity of the machine learning technology which allows to create effective models assuming that the number of features is much smaller than the number of cases based on which the model is created. The median calculation described above also reduces the dimensionality of the feature space but determining aggregation parameters in the context of determined subperiods is of primary importance. Aggregation parameters or aggregation attributes used in the present disclosure should be understood as parameters determined on the basis of measurement values collected (aggregated) in a given subperiod. In the described embodiment, the above process was carried out in full consultation with a field expert who, based on the knowledge of physiological processes described by the data, was able to point to the characteristic elements in the daily profile of the parameter value of the eyeball biorhythm (hereinafter also referred to as TF). As a result of these actions the features described below were determined which in the described embodiment of the invention were subsequently used to create statistical models minimizing the classification error gradient by means of boosting and logistic regression models:

a) Sum of the Area Under the TF Curve in a Subperiod

This sum is calculated assuming a constant TF level between successive recorded values/measurements (step curve) in a subperiod. For the selected (e.g. TP1—SLEEP) subperiod $T=\{t_0, t_1, \ldots, t_n\}$ TF measurements $\{tf_0, tf_1, \ldots, tf_n\}$ are stored. The sum of the area under the TF curve is equal to the sum of rectangles for individual measurements, i.e.

$$S_T = \sum_{i=0}^{i=n-1} s_i, \text{ where } s_i = (t_{i+1} - t_i)\cdot tf_1$$

b) Slope Angle of a Linear Regression Line in a Subperiod

The slope angle of a linear regression line for TF measurements in a subperiod is calculated by the method of least squares. Initial time $t_0=0$ is assumed for each one of the subperiod. The original directional coefficient of the line or the angle value in radians is recorded. The least squares method determines coefficients $\beta=(\beta_0, \beta_1)$ of the line equation on the plane according to formula $\beta=(X^TX)^{-1}X^Ty$, for the input data matrix X written with 1 at the first position.

c) Total Variation in a Subperiod

The total variation in a subperiod is calculated in the form of the numerical integral of the second derivative. For example, the total variation of TF overtime period T can be calculated from the formula:

$$V_T = \sum_{i=0}^{i=n-1} |tf_{i+1} - tf_i|$$

d) Representative Values of the Discrete Fourier Transform (FFT)

The discrete Fourier transform is calculated by the FFT method based on the original data from which the linear trend has been removed. Representative FFT values are determined using cluster analysis that uses the DTW (Dynamic Time Warping) metric:

i. power of the first FFT local maximum taking into account main components (Power_1)

ii. frequency of the first FFT local maximum taking into account main components (Hz_1)

For the DFT calculation in the present embodiment of the invention, the fft method from stats v3.6.2 package in R was used: (https://www.rdocumentation.org/packages/stats/versions/3.6.2/topics/fft).

String $\{X_k\}=X_0, X_1, \ldots, X_{N-1}$ of the DFT values is calculated for input string $\{x_n\}=x_0, x_1, \ldots, x_{N-1}$ according to the formula:

$$X_k = \sum_{n=0}^{N-1} x_n \cdot e^{-\frac{i2\pi}{N}kn}, \text{ where } k = 0, 1, \ldots, N-1.$$

Due to disturbances in the exact profile of the eyeball biorhythm during the day associated with the subject's blinking, the described FFT parameters are preferably calculated only for subperiod TP2—WAKE (sleep).

e) Correlations Between Eyeball Biorhythm Values and Cardiovascular Parameter Values in the Determined Subperiods In the present embodiment of the invention, correlations between median values of TF parameters and medians of individual cardiovascular system parameters (SAP, DAP, MAP, HR, SPO2, CO) were determined within each subperiod. In general, the correlation calculation can be performed using generally known and available statistical models. In the present embodiment, the correlation calculation was carried out using methods from the psych v1.8 package for the R language.

The Spearman's rank correlation coefficients were calculated using the corr.test method assuming a standard threshold of 0.05 for (alpha) parameter defining the range of confidence intervals. The application of this method minimizes the impact of separated values/measurements (outliers) on the determined correlation coefficients for the analysed parameters. The determined coefficients belong to interval [−1.1] whose endpoints correspond to the total negative and total positive correlation.

The method of calculating correlations is described in more detail below. For n measurements, the original vectors X, Y of length n are converted into rank vectors $X^{rg}$, $Y^r$. In the simplest case where there are no identical measurements, it can be assumed that rank vectors are indexes of ordered/sorted original vectors. In the case of repetitions of certain values, a procedure assigning rational ranks is used which resolves the ambiguity of the ranking.

$$\text{rho}=\text{Cov}(X^{rg},Y^{rg})/(\sigma(X^{rg})\cdot\sigma(Y^{rg})),$$

where rho—Spearman's correlation coefficient, Cov—rank vector covariance, G—standard deviation of the rank vector.

rho coefficient is equal to ±1 when the relationship between X, Y is a monotonic function. In the case of Pearson's correlation, the corresponding coefficient is equal to ±1 when the relationship between X, Y is a linear function. The correlation sign specifies the type of relationship between X, Y—it is positive for an increasing function and negative for a decreasing function.

The process ends with returning a result in the numerical form and possibly in the graphic form, such as a heat map. When generating a heat map, similar correlation results are additionally grouped (clustering) to visually gather subjects into groups with similar characteristics. The heat map may be helpful for the physician when making a diagnosis, but it is not required for the functioning of solutions according to the invention. Below a table showing the numerical values of correlation between the cardiovascular system parameters (median_DAP, median_HR, median_SAP, median_MAP, median_SpO2, median_CO) and the eyeball biorhythm (TF) parameters for SLEEP—WAKE subperiod is presented.

TABLE 1

Numerical values of correlation between the cardiovascular system parameters and the eyeball biorhythm parameters for SLEEP-WAKE subperiod

| ID | median_DAP | median_HR | median_SAP | median_MAP | median_SpO2 | median_CO |
|---|---|---|---|---|---|---|
| tf_001 | 0 | 0.41 | 0.3 | 0 | 0 | 0.48 |
| tf_002 | −0.73 | −0.51 | −0.8 | −0.77 | 0 | −0.72 |
| tf_003 | −0.4 | −0.55 | −0.55 | −0.54 | 0 | −0.62 |
| tf_004 | −0.37 | 0 | −0.34 | −0.39 | 0 | 0 |
| tf_005 | −0.65 | 0 | −0.48 | −0.59 | 0 | 0 |
| tf_006 | −0.69 | −0.67 | −0.56 | −0.69 | 0 | −0.57 |
| tf_007 | −0.61 | 0 | −0.82 | −0.71 | 0 | −0.42 |
| tf_008 | −0.73 | −0.5 | −0.66 | −0.71 | −0.35 | −0.5 |
| tf_009 | −0.29 | −0.82 | 0 | 0 | 0 | −0.76 |
| tf_010 | −0.6 | 0.34 | −0.56 | −0.6 | 0 | 0.44 |
| tf_011 | 0 | −0.3 | 0 | 0 | 0 | 0 |
| tf_012 | 0 | 0 | 0 | 0 | 0 | 0 |
| tf_013 | −0.37 | 0 | −0.33 | −0.35 | 0 | 0 |
| tf_014 | 0 | 0 | 0 | 0 | 0 | 0 |
| tf_015 | 0 | 0 | −0.33 | −0.32 | 0.39 | 0 |
| tf_016 | −0.29 | −0.45 | −0.37 | −0.34 | 0 | −0.44 |
| tf_017 | 0 | 0 | 0 | 0 | 0 | 0 |
| tf_018 | −0.71 | −0.44 | −0.75 | −0.77 | 0 | −0.49 |
| tf_019 | −0.33 | −0.58 | 0 | 0 | 0 | −0.39 |
| tf_020 | −0.37 | −0.31 | −0.28 | −0.33 | 0 | 0 |
| tf_021 | −0.69 | 0 | −0.67 | −0.68 | 0 | 0 |
| tf_022 | −0.45 | −0.26 | −0.53 | −0.51 | −0.56 | −0.46 |
| tf_023 | −0.59 | −0.3 | −0.47 | −0.55 | −0.4 | −0.33 |
| tf_024 | −0.48 | −0.31 | −0.48 | −0.48 | 0.3 | −0.33 |
| tf_025 | 0.64 | 0.58 | 0.52 | 0.6 | 0.43 | 0.4 |
| tf_026 | −0.69 | 0.72 | 0 | −0.61 | −0.57 | 0.82 |
| tf_027 | −0.37 | 0 | −0.32 | −0.36 | 0 | 0 |
| tf_028 | 0 | 0 | 0 | 0 | 0 | 0 |
| tf_029 | −0.39 | 0 | −0.28 | −0.33 | 0.31 | 0 |
| tf_030 | −0.73 | −0.72 | −0.79 | −0.76 | 0 | −0.65 |
| tf_031 | −0.65 | −0.37 | −0.61 | −0.65 | 0 | −0.34 |

Figure 6:
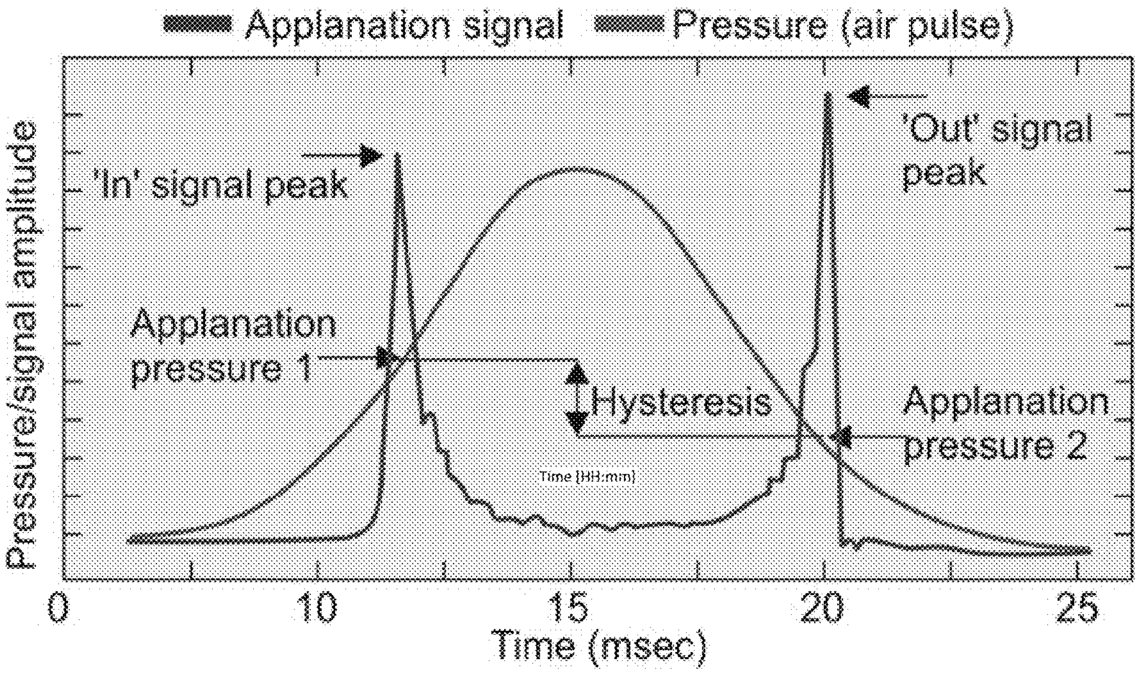
FIG. 6 shows a signal amplitude/pressure relationship as a function of time using the ocular response analyser.

As mentioned at the beginning, when creating a predictive model, in step s103*c* additional parameters can be optionally considered such as subject's age, corneal hysteresis and corneal resistance factor described below with reference to FIG. 6 which shows a signal amplitude/pressure relationship as a function of time using the ocular response analyser.

a) Subject's age—a parameter specifying subject's age at the time of diagnosing.

b) Corneal hysteresis (CH) is an in vivo measurement of cornea biomechanical properties and an independent risk factor for the development and progression of glaucoma neuropathy. Its value reflects the capacity of the corneal tissue to dissipate energy. Corneal hysteresis determines whether the eyeball wall absorbs energy associated with intraocular pressure fluctuations, increasing the risk of lamina cribosa sclerae reconstruction and damage to the optic nerve, or it is able to dissipate this force, protecting the above eye structures from excessive biomechanical loads. Simply put, CH reflects the ability to cushion of the eyeball wall. Eyes that are good shock absorbers (high CH) are less likely to develop glaucoma neuropathy and less often experience its progression. Conversely, poorly cushioning (low CH) eyes are more likely to develop glaucoma and glaucoma is more likely to progress. Average CH for the population for most ethnic groups is around 10 mmHg.

Corneal hysteresis is a numerical value that is automatically generated when performing a measurement by the ORA (Ocular Response Analyser) from Reichert. This device functions very much like a noncontact tonometer. A metered puff of air is delivered to the cornea, flattening it into an applanation configuration (maximum flattening). Then the air puff continues to deform the cornea past this point resulting in a transitory concave corneal configuration. As the pressure of the air puff diminishes, the cornea returns to its normal configuration, passing from the concave configuration, through the applanation position (maximum flattening) to the convex configuration. The pressure of the air puff at the point of the first and second applanations is different (being lower during the second), as the cornea's viscoelastic nature dissipates some of the energy. The difference in IOP at each of these two applanation points is defined as the corneal hysteresis. If the cornea were perfectly elastic and did not dampen some of the energy, the two applanation points would occur at the same IOP level.

c) Corneal resistance factor (CRF)

The CRF is derived from the formula (P1-kP2) where k is the constant determined from an empirical analysis of the relationship between P1 (first applanation pressure), P2 (second applanation pressure) and CCT (central corneal thickness). The CRF describes corneal resistance—its elastic properties. CRF is believed to represent corneal elasticity, with stronger correlations with IOP and CCT compared to CH.

Based on a set of data concerning subjects who were diagnosed, a predictive model is created. For this purpose a record is created in step s104 for each of the diagnosed patients, the record containing the features determined in step s103*a* as well as optionally the features determined in steps s103*d* and/or s103*c*.

Where appropriate, a specific subset can be selected from all the determined features to be used in subsequent steps of the method. Extracting features that from the point of view of the created model can contribute to increase its effectiveness, can occur as a result of testing various combinations of features. In this case, the significance of the features that affect the result in a given iteration is taken into account. Exemplary techniques and/or metrics to evaluate the effectiveness of models created based on various combinations of features are indicated and described later in this disclosure.

An exemplary record created for the described embodiment is presented below which also uses additional optional features. In addition, for a better understanding of the record, the middle column "feature description" contains explanation of particular parameters but this column is not part of the created record.

| Feature name | Feature description | Value |
|---|---|---|
| AGE | Age | 46.00 |
| CH | Corneal hysteresis | 8.30 |
| CRF | Corneal resistance factor | 8.80 |
| tp2_wake_median_HR | Spearman's correlation coefficient for attribute values of TF and HR in subperiod tp2-wake | 0.00 |
| tp2_wake_median_DAP | Spearman's correlation coefficient for attribute values of TF and DAP in subperiod tp2-wake | 0.00 |
| start_tp1_median_MAP | Spearman's correlation coefficient for attribute values of TF and MAP in subperiod start-tp1 | 0.00 |
| sleep_tp2_median_SAP | Spearman's correlation coefficient for attribute values of TF and SAP in subperiod sleep-tp2 | 0.00 |
| tp3_end_median_CO | Spearman's correlation coefficient for attribute values of TF and CO in subperiod tp3-end | 0.00 |
| start_tp1_rawTF_sum | Area under the TF curve in subperiod start-tp1 | 88660.83 |
| tp1_sleep_rawTF_sum | Area under the TF curve in subperiod tp1-sleep | 77579.86 |
| sleep_tp2_rawTF_sum | Area under the TF curve in subperiod sleep-tp2 | 91247.26 |
| tp2_wake_rawTF_sum | Area under the TF curve in subperiod tp2-wake | 93400.43 |
| wake_tp3_rawTF_sum | Area under the TF curve in subperiod wake-tp3 | 190358.86 |
| tp3_end_rawTF_sum | Area under the TF curve in subperiod tp3-end | 160358.86 |
| start_tp1_SAP_sum | Area under the SAP curve in a given subperiod | 2313300.00 |
| tp1_sleep_SAP_sum | Area under the SAP curve in a given subperiod | 1990800.00 |
| sleep_tp2_SAP_sum | Area under the SAP curve in a given subperiod | 1049400.00 |
| tp2_wake_SAP_sum | Area under the SAP curve in a given subperiod | 1018500.00 |
| wake_tp3_SAP_sum | Area under the SAP curve in a given subperiod | 929400.00 |
| tp3_end_SAP_sum | Area under the SAP curve in a given subperiod | 2211300.00 |
| start_tp1_DAP_sum | Area under the DAP curve in a given subperiod | 1575000.00 |
| tp1_sleep_DAP_sum | Area under the DAP curve in a given subperiod | 1278900.00 |
| sleep_tp2_DAP_sum | Area under the DAP curve in a given subperiod | 574800.00 |
| tp2_wake_DAP_sum | Area under the DAP curve in a given subperiod | 587100.00 |
| wake_tp3_DAP_sum | Area under the DAP curve in a given subperiod | 528300.00 |
| tp3_end_DAP_sum | Area under the DAP curve in a given subperiod | 1323300.00 |
| start_tp1_MAP_sum | Area under the MAP curve in a given subperiod | 1811400.00 |
| tp1_sleep_MAP_sum | Area under the MAP curve in a given subperiod | 1510500.00 |
| sleep_tp2_MAP_sum | Area under the MAP curve in a given subperiod | 728400.00 |
| tp2_wake_MAP_sum | Area under the MAP curve in a given subperiod | 727500.00 |
| wake_tp3_MAP_sum | Area under the MAP curve in a given subperiod | 660300.00 |
| tp3_end_MAP_sum | Area under the MAP curve in a given subperiod | 1614000.00 |
| start_tp1_SAP_slope | Regression line slope of the SAP values in a given subperiod | −0.000786 |
| tp1_sleep_SAP_slope | Regression line slope of the SAP values in a given subperiod | 0.000615 |
| sleep_tp2_SAP_slope | Regression line slope of the SAP values in a given subperiod | 0.002841 |
| tp2_wake_SAP_slope | Regression line slope of the SAP values in a given subperiod | −0.002833 |
| wake_tp3_SAP_slope | Regression line slope of the SAP values in a given subperiod | 0.001666 |
| tp3_end_SAP_slope | Regression line slope of the SAP values in a given subperiod | −0.001515 |
| start_tp1_DAP_slope | Regression line slope of the DAP values in a given subperiod | −0.000146 |
| tp1_sleep_DAP_slope | Regression line slope of the DAP values in a given subperiod | 0.000175 |
| sleep_tp2_DAP_slope | Regression line slope of the DAP values in a given subperiod | 0.003079 |
| tp2_wake_DAP_slope | Regression line slope of the DAP values in a given subperiod | −0.001222 |
| wake_tp3_DAP_slope | Regression line slope of the DAP values in a given subperiod | 0.002444 |
| tp3_end_DAP_slope | Regression line slope of the DAP values in a given subperiod | −0.002286 |
| start_tp1_MAP_slope | Regression line slope of the MAP values in a given subperiod | −0.000362 |
| tp1_sleep_MAP_slope | Regression line slope of the MAP values in a given subperiod | 0.000315 |
| sleep_tp2_MAP_slope | Regression line slope of the MAP values in a given subperiod | 0.003063 |
| tp2_wake_MAP_slope | Regression line slope of the MAP values in a given subperiod | −0.001777 |

-continued

| Feature name | Feature description | Value |
|---|---|---|
| wake_tp3_MAP_slope | Regression line slope of the MAP values in a given subperiod | 0.002222 |
| tp3_end_MAP_slope | Regression line slope of the MAP values in a given subperiod | −0.002029 |
| start_tp1_TF_sec_deriv_integral | Total variation of the scaled TF in a given subperiod | 0.004761 |
| tp1_sleep_TF_sec_deriv_integral | Total variation of the scaled TF in a given subperiod | 0.009872 |
| sleep_tp2_TF_sec_deriv_integral | Total variation of the scaled TF in a given subperiod | −0.003252 |
| tp2_wake_TF_sec_deriv_integral | Total variation of the scaled TF in a given subperiod | −0.006620 |
| wake_tp3_TF_sec_deriv_integral | Total variation of the scaled TF in a given subperiod | −0.040998 |
| tp3_end_TF_sec_deriv_integral | Total variation of the scaled TF in a given subperiod | 0.000116 |
| start_tp1_rawTF_sec_deriv_integral | Total variation of the original TF in a given subperiod | −0.002090 |
| tp1_sleep_rawTF_sec_deriv_integral | Total variation of the original TF in a given subperiod | 0.004761 |
| sleep_tp2_rawTF_sec_deriv_integral | Total variation of the original TF in a given subperiod | 0.009872 |
| tp2_wake_rawTF_sec_deriv_integral | Total variation of the original TF in a given subperiod | −0.003252 |
| wake_tp3_rawTF_sec_deriv_integral | Total variation of the original TF in a given subperiod | −0.006620 |
| tp3_end_rawTF_sec_deriv_integral | Total variation of the original TF in a given subperiod | −0.040998 |
| start_tp1_SAP_sec_deriv_integral | Total variation of the SAP values in a given subperiod | 0.010350 |
| tp1_sleep_SAP_sec_deriv_integral | Total variation of the SAP values in a given subperiod | 0.058333 |
| sleep_tp2_SAP_sec_deriv_integral | Total variation of the SAP values in a given subperiod | −0.052361 |
| tp2_wake_SAP_sec_deriv_integral | Total variation of the SAP values in a given subperiod | −0.044305 |
| wake_tp3_SAP_sec_deriv_integral | Total variation of the SAP values in a given subperiod | −0.094736 |
| tp3_end_SAP_sec_deriv_integral | Total variation of the SAP values in a given subperiod | −0.038518 |
| start_tp1_DAP_sec_deriv_integral | Total variation of the DAP values in a given subperiod | −0.057925 |
| tp1_sleep_DAP_sec_deriv_integral | Total variation of the DAP values in a given subperiod | −0.045490 |
| sleep_tp2_DAP_sec_deriv_integral | Total variation of the DAP values in a given subperiod | −0.019444 |
| tp2_wake_DAP_sec_deriv_integral | Total variation of the DAP values in a given subperiod | 0.042777 |
| wake_tp3_DAP_sec_deriv_integral | Total variation of the DAP values in a given subperiod | 0.030555 |
| tp3_end_DAP_sec_deriv_integral | Total variation of the DAP values in a given subperiod | −0.070175 |
| start_tp1_MAP_sec_deriv_integral | Total variation of the MAP values in a given subperiod | −0.057925 |
| tp1_sleep_MAP_sec_deriv_integral | Total variation of the MAP values in a given subperiod | −0.136470 |
| sleep_tp2_MAP_sec_deriv_integral | Total variation of the MAP values in a given subperiod | −0.007777 |
| tp2_wake_MAP_sec_deriv_integral | Total variation of the MAP values in a given subperiod | 0.042777 |
| wake_tp3_MAP_sec_deriv_integral | Total variation of the MAP values in a given subperiod | 0.012222 |
| tp3_end_MAP_sec_deriv_integral | Total variation of the MAP values in a given subperiod | −0.031578 |

In step s105 a label indicating a diagnosis made by a medical specialist (diseased/healthy) is assigned to each record (i.e. a set of features describing a single subject). As a result of gathering many such records created analogously for each of the many examined subjects a learning set is obtained which is used by the methods of supervised machine learning to construct a predictive model. In the described embodiment, the learning set was created on the basis of 120 records created for each of 120 subjects, who were examined and appropriately diagnosed by a medical specialist.

The predictive model is created in step s106 using supervised machine learning mechanisms. The term supervised machine learning mechanisms used in this description should be understood as one or more algorithms, such as regression algorithms, e.g. Generalized Linear Model (GLM), decision tree algorithms), Bayesian algorithms e.g. Naive Bayes, ensemble algorithms e.g. Gradient Boosting Machine, support vector-based algorithms (SVM). It is not an exhaustive list and the skilled person in the art will also notice similar algorithms that can be equally used, although they are not specifically mentioned here. Details and rules of functioning of the mentioned algorithms have already been widely described in the literature, so for the sake of clarity they are not discussed in detail here. Examples of literature items:

- Pattern Recognition and Machine Learning; Christopher Bishop; Springer 2006
- Applied Predictive Modeling; Kjell Johnson, Max Kuhn; Springer 2013
- The Elements of Statistical Learning, 2nd edition; T. Hastie, R. Tibshirani; Springer 2008
- Python Machine Learning; S. Raschka, Packt Publishing 2015

In other words, the most important contribution of the present invention is the feature set which is determined in accordance with the principles described above and which constitutes the set of input data. Based on this input data, it is possible to create a predictive model using any appropriate supervised machine learning techniques, examples of which are indicated above. The selection of appropriate algorithms is therefore of secondary nature and can be carried out in many different ways and in various combinations obvious to those skilled in the art.

In the described embodiment, in order to create a predictive model, two algorithms from the above non-limiting list of supervised machine learning algorithms were selected and used: Generalized Linear Model (GLM) and Gradient Boosting Machine (GBM). Below, these algorithms are described in more detail in terms of their use in the described example, however, it should be noted that the invention is not limited to the indicated combination.

GLM (Generalized Linear Model) are generalized linear models with binomial distribution (equivalent to logistic regression). Models in this class use the properties of the logistic function to estimate the probability in binary classification. Below details of logistic regression are described that can be helpful for understanding the present invention.

For the binomial distribution (classification labels from the set {0,1}, where 0–NORM) a probability model (a posteriori) P (C=c|X=x) is built with the following properties:

$$P(C=0\mid X=x)=\frac{\exp(\beta_0+\beta^T X)}{1+\exp(\beta_0+\beta^T x)}\text{ and}$$

-continued $$P(C=1 \mid X=x)=\frac{1}{1+\exp(\beta_0+\beta^T x)}.$$

The monotonic transformation in this case is a so-called logit: log (p/(1−p)). Accordingly:

$$\log\frac{P(C=0 \mid X=x)}{P(C=1 \mid X=x)}=\beta_0+\beta^{T_x}.$$

The hyperplane separating classes is a set of points {x: $\beta_0+\beta^T x=0$}

The logistic regression model is fitted to the input data using the maximum likelihood method. Maximum reliability for N observations is given by the general formula $$I(\theta)=\sum_{i=1}^{N}\log p_{g_i}(x_i;\theta), \text{ where } p_k(x_i;\theta)=P(G=k|X=x;\theta)$$

In the case of binomial distribution, in order to maximize I(β), zeros of derivative $$\frac{\partial l(\beta)}{\partial\beta}=\sum_{i=1}^{N}x_i(y_i-p(x_i;\beta))=0 \text{ (formula for binomial distribution – labels \{0, 1\}) are found.}$$

GBM (Gradient Boosting Machine) is a sequential committee/series of classifiers minimizing classification errors, with variable weight of committee components. This method uses a weighted average to calculate the final result, where the reduced dependence of the classifier components is obtained by random drawing subsets of training variables. GBM (Gradient Boosting Machine) algorithm is based on decision trees that divide the data space into separate square subsets. For each of these subsets, a dividing strategy is used that minimizes the mean square error (MSE) of the prediction $$\sum_{i=1}^{N}(y_i-\overline{y_i})^2,$$

where $\overline{y}_i$ is an estimated classification of the i-th observation. Subsequent decision trees hi are iteratively built, the algorithm result is the sum of trees from the generated string:

$$F_m(x)=F_{m-1}(x)+\gamma_m h_m(x)$$

where the coefficient $\gamma_m \in (0,1]$ is the weight of the generated tree (learning rate) added to the string/committee.

The next decision tree in the m-th iteration is generated for the remainder obtained in the previous iteration R(x)=f (x)−$F_{m+1}$(x). The error (represented by the loss function) is minimized by the method of the steepest gradient descent for the selected loss function (e.g. square error).

In step s107, classification models are created for the selected subset of attributes using 10-fold cross-validation to assess the accuracy of the prediction. Cross-validation (CV) is a model validation method that allows to assess the prediction error, and therefore allows to assess how effective the created model is. Accordingly, cross-validation can be used, for example, as a tool to compare models based on specific combinations of features and/or combinations of algorithms to identify the most advantageous configuration of the predictive model.

In the case of k-fold cross-validation, the input data set is randomly divided into k equal subsets. In iteration from 1 to k, another subset is selected that will be the test set. The remaining k−1 subsets are combined and used as a training set to create the model. The generated results (for selected error measures) of cross validation (k numbers) are finally averaged (average or median) to estimate the prediction error of the model (with determined parameters and attributes).

The following metrics were used to evaluate binary models/classifiers:

Accuracy: Accuracy=(TP+TN)/(number of all cases), where TP—true positive +, TN—true negative − logistic loss function (log loss)

AUC (area under the ROC curve)

mean square error (MSE)

In order to assess the variance/standard deviation of the cross-validation results, 50 iterations were performed for the procedure of calculating the above mentioned metrics.

AUC (Area Under the Curve) is the area under the ROC (Receiver Operating Characteristic) curve and it represents the accuracy of prediction based on sensitivity (TPR—true positive rate) and 1—specificity (FPR—false positive rate). The classifier specificity is the TNR (true negative rate) equal to the ratio of the number of subsets of cases classified as negative from the set of negative cases). The ROC curve maps parametrically TPR(t) to FPR(t) for the variable parameter t, a so-called cut-off point. AUC of the ideal model is 1. The model providing the inversion of the reference classification has AUC equal to 0.

The logarithmic loss function (log loss) is a measure of the accuracy of prediction, which tends slowly to 0 for the model approaching the ideal pattern. In the case of incorrect predictions, the value of L increases.

$$L(y,\overline{y})=-y\cdot\log(\overline{y})-(1-y)\log(1-\overline{y})$$

where prediction $\overline{y} \in [0,1]$. For the test set, the average of $L(y,\overline{y})$ of individual elements of this set is calculated.

MSE (Mean Squared Error) is a measure of the accuracy of model predictions that corresponds to the mean squared of deviations of the prediction from the correct value.

$$SE=\frac{1}{N}\sum_{i=1}^{N}(y_i-\overline{y}_i)^2,$$

where $\overline{y}_i$—estimated classification of the i-th observation, $y_i$—correct classification of the i-th observation.

Examples of models created using GLM, GBM algorithms for various sets of attributes (versions 1 to 4) with their effectiveness measures are presented below:

| | Attributes | AUC | MSE | Log loss |
|---|---|---|---|---|
| Version 1 | "CH", "CRF", "AGE", "tp2_wake_median_HR", "sleep-tp1_rawTF_sec_deriv_integral", "wake_tp3_rawTF_sum" | 0.89 ± 0.022 | 0.09493394 ± 0.016 | 1.792935 ± 0.4985968 |
| Version 2 | "CH", "CRF", "tp2_wake_median_HR", "sleep-tp1_rawTF_sec_deriv_integral", "wake_tp3_rawTF_sum" | 0.88 ± 0.015 | 0.1311883 ± 0.011 | 0.5147769 ± 0.06530407 |
| Version 3 | "CH", "tp1_sleep_median_MAP", "AGE", "tp2_wake_median_HR", "sleep-tp1_rawTF_sec_deriv_integral", "wake_tp3_rawTF_sum" | 0.94 ± 0.017 | 0.095 ± 0.022 | 1.837 ± 0.528 |
| Version 4 | tp1_sleep_median_MAP", "tp2_wake_median_HR", "sleep-tp1_rawTF_sec_deriv_integral", "wake_tp3_rawTF_sum" | 0.91 ± 0.028 | 0.114 ± 0.019 | 0.618 ± 0.538 |

where CH is corneal hysteresis, CRF is corneal resistance factor, AGE is the subject's age, tp2_wake_median_HR is the Spearman's correlation coefficient for attribute values of TF and HR in subperiod TP2—WAKE, sleep-tp1_rawTF_sec_deriv_integral is the total variation of the SAP values in subperiod SLEEP—TP1, wake_tp3_rawTF_sum is the area under the curve of TF profile in subperiod WAKE—TP3, tp1_sleep_median_MAP is the correlation coefficient for coefficient parameters of TF and MAP in subperiod TP1—SLEEP.

The predictive model for which the construction method is described above is used to classify subjects by an inventive device. Similar to the construction of the predictive model, the data describing a subject being examined must be processed to obtain a set of corresponding features (the same features as the ones used in the model). Then the model is run on this data set and in consequence a result is generated in the form of allocation to one of the groups: diseased, healthy, along with the probability of this prediction.

The proposed solution can be used in an intelligent physician decision support system which will allow for an ultra-early assessment of the risk of developing glaucoma neuropathy and to describe its factors in the population of people observed for glaucoma, subjects with a positive family history and ocular hypertension. Furthermore, the system will enable personalization of local and systemic therapy in glaucomatous subjects, indicating individual risk factors for disease progression.

Figure 7:
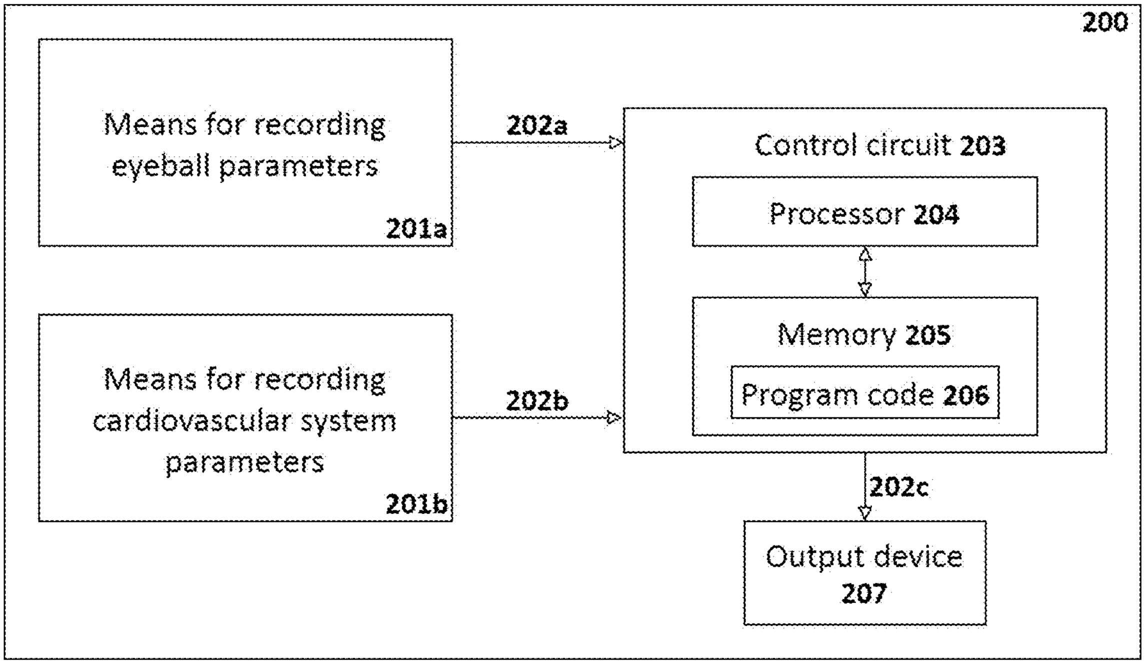
FIG. 7 shows a schematic block diagram of an exemplary device for predicting glaucoma risk in a subject.

FIG. 7 shows a schematic block diagram of an exemplary device for implementing the method for creating a predictive model and the method for predicting glaucoma risk in a subject according to the invention. The device 200 comprises a control circuit 203 in which a processor 204 and a memory 205 are installed, the memory 205 being operatively coupled to the processor 204. To the control circuit 203 means 201*a* and means 201*b* are coupled that are adapted to recording subject's eyeball parameters and cardiovascular system parameters, respectively. As the means 201*a* and 201*b* any suitable means can be used such as, e.g., the systems described above. These means record time profiles of parameters of the examined subject which are sent to the control circuit 203 via connections 202*a* and 202*b* and stored in the memory 205. Furthermore, in the memory 205 a program code 206 is stored which, when executed by the processor 204, causes the implementation of the subsequent steps of the above-described methods. The result of the processing performed by the processor in the form of classification of the examined subject as diseased or healthy along with determined probability is transmitted via connection 202*c* to an output device 207 such as a display or monitor screen which presents the said result and other information related to the parameters and/or features determined from the profiles provided by the means 201*a* and 201*b* (such as correlation parameters, correlation heat maps etc. determined during creation of the predictive model) e.g. to a physician so that he can take them into account e.g. during diagnosis and select appropriate treatment. Optionally, an input device (not shown) may also be provided, such as a keyboard or pointing device, connected to the control circuit 203, which will allow for the selection of the desired data to be presented by the output device 207.

In a particular embodiment of the device 200 according to the invention, the means 201*a* and 201*b* and/or the output device 207 are arranged in a remote location relative to the control circuit 203. In such case, the respective connections 202*a*, 202*b* and/or 202*c* are implemented as communication network connections, e.g. Internet network connections. This provides greater flexibility in the use of the device 200 according to the invention. For example, in one possible scenario, a subject uses means 201*a* and 201*b* for recording the described parameters which during recording are collected in a local memory of the means 201*a* and 201*b*, and then, once the data collection is completed, the collected data is sent automatically or by a person helping to carry out the examination, for example via a dedicated network connection, to the control circuit 203 implemented e.g. in the form of a server. Once the data is processed by the control circuit 203, the result can be sent back to the output device 207, e.g. for presentation to a person carrying out the examination (e.g. a physician).

The following numbered embodiments are contemplated and non-limiting:

1. A method (100) for creating a predictive model for predicting glaucoma risk in a subject, the method comprising:
   a step of creating a diagnostic model comprising, for each one of a plurality of subjects:
   a) recording (s101*a*) a 24-hour profile of eyeball parameters;
   b) dividing (s102*a*) the recorded 24-hour profile of eyeball parameters at least into subperiods:
      an initial subperiod (START—TP1);
      a subperiod preceding assuming a horizontal position for sleep (TP1—SLEEP);
      a subperiod following assuming a horizontal position for sleep (SLEEP—TP2);
      a subperiod preceding assuming a vertical position after sleep (TP2—WAKE);
      a subperiod following assuming a vertical position after sleep (WAKE—TP3);

a final subperiod (TP3—END);

c) determining (s103*a*), in each subperiod, features describing a single subject in the form of at least one aggregating attribute;

d) creating (s104) a record containing the determined features describing a single subject;

e) assigning (s105) a label indicating a diagnosis (diseased/healthy) made by a physician to the created record; and a step of creating a predictive model, based on a set of records created for the plurality of subjects, using supervised machine learning mechanisms based on one or more algorithms selected at least from regression algorithms, decision trees, Bayesian algorithms, ensemble algorithms and support vector-based algorithms.

2. The method according to clause 1, wherein the predictive model is created using 10-fold cross-validation.

3. The method according to clause 1 or 2, wherein the aggregating attributes are selected from a group including: a sum of the area under the curve in a subperiod, the slope angle of a linear regression line in a subperiod, the total variation in a subperiod, representative values of the discrete Fourier transform in a subperiod.

4. The method according to any one of the preceding clauses, wherein the eyeball parameters are selected from a group including: the circumference at the corneoscleral limbus of an eyeball and intraocular pressure.

5. The method according to any one of the preceding clauses, wherein:

simultaneously with recording (s101*a*) the 24-hour profile of eyeball parameters in step (s101*b*) of the method (100) cardiovascular system parameters are recorded, in the subperiods determined in step (s102*a*) of the method (100) correlations between the eyeball parameters and the cardiovascular system parameters are calculated (s103*b*), to the record describing a single subject created in the step (s104) of the method (100) the calculated correlation parameters are appended as further features.

6. The method according to clause 5, wherein the cardiovascular system parameters are selected from a group including: blood pressure (BP): systolic arterial pressure (SAP), diastolic arterial pressure (DAP), mean arterial pressure (MAP), heart rate (HR), oxygen blood saturation (SpO2) and cardiac output fraction calculated according to the formula: CO=[(SAP−DAP)/SAP+DAP)]×HR.

7. The method according to any one of the preceding clauses, wherein one or more additional features selected from a group including: subject's age, corneal resistance factor and corneal hysteresis are determined (s103*c*) and appended to the record describing a single subject created in the step (s104) of the method (100).

8. The method according to any one of the preceding clauses, wherein the record describing a single subject in the step (s104) of the method (100) is limited to a selected subset of the all determined features.

9. The method according to any one of the preceding clauses, wherein the determined subperiods furthermore include a subperiod from the session start to assuming a horizontal position for sleep (START-SLEEP) and/or a subperiod from assuming a horizontal position for sleep to assuming a vertical position after sleep (SLEEP—WAKE) and/or a subperiod from assuming a horizontal position at 14:00 to assuming a vertical position at 15:30 with sustained consciousness (TIME 14:00-TIME 15:30).

10. The method according to any one of the preceding clauses, wherein the boundaries defining particular subperiods are as follows:

TP1: 5 hours before assuming a horizontal position for sleep,

TP2: assuming a horizontal position for sleep+2 hours,

TP3: assuming a vertical position after sleep+2 hours.

11. A method for determining glaucoma risk in a subject, the method comprising:

creating, for a patient to be examined, a record containing the same feature set as the one created in the step (s104) of the method (100) for creating a predictive model, determining an allocation of the subject to a group of diseased or healthy subjects with determined probability using the predictive model created according to the method of any one of clauses 1-10.

12. A device for predicting glaucoma in a subject, comprising:

means (201*a*) for recording eyeball parameters;

means (201*b*) for recording cardiovascular system parameters;

a control circuit (203) having a communication connection (202*a*, 202*b*) with the means (201*a*, 201*b*);

a processor (204) installed in the control circuit (203);

a memory (205) installed in the control circuit (203) and operatively coupled to the processor (204);

an output device (207) for presenting results having a communication connection (202*c*) with the control circuit (203);

wherein the processor (204) is configured to execute a program code (206) stored in the memory (205) for performing steps of the method as defined in any one of clauses 1-10 and of the method as defined in clause 11 based on data provided by the means (201*a*, 201*b*).

13. The device according to clause 12, wherein the means (201*a*) for recording eyeball parameters, the means (201*b*) for recording cardiovascular system parameters and/or the output device (207) are arranged in a remote location with respect to the control circuit (203), and the communication connections (202*a*, 202*b*, 202*c*) are communication network connections.

14. A computer program comprising a program code for performing steps of the method as defined in clauses 1-10 and of the method as defined in clause 11.

15. A computer readable medium on which the computer program of clause 14 is stored.

Although the invention has been described in detail with reference to the specific embodiments set out above, this description is by way of example and is not intended to limit the invention to specific embodiments. The skilled person will appreciate that various changes and modifications are possible without departing from the scope of the invention as defined by the following claims.

The invention claimed is:

1. A method for creating a predictive model for predicting glaucoma development and/or progression risk in a subject using a device including a processor and a memory, the method comprising:

a) a step of obtaining, from each one of a plurality of subjects, a measurement data series by recording a 24-hour profile of eyeball parameters by an eyeball parameters measuring and recording device configured to obtain the eyeball parameters continuously or at intervals over a 24-hour period, wherein the eyeball parameters include a circumference at a corneoscleral limbus of an eyeball and/or an intraocular pressure, and simultaneously recording, for each one of the plurality of subjects, cardiovascular system parameters by a cardiovascular system parameters measuring and recording device configured to obtain the cardiovascular system parameters continuously or at intervals over the 24-hour period, the cardiovascular system parameters including a systolic arterial pressure, a diastolic arterial pressure, a mean arterial pressure, and a heart rate, and storing data recorded by the recording devices in the memory;

b) a step of applying, for each of the measurement data series, a procedure of dividing the recorded 24-hour profile of eyeball parameters into subperiods, by the processor that retrieves the recorded data from the memory, wherein said procedure comprises:

identifying, for the recorded 24-hour profile of eyeball parameters, reference time points including: session start (START) and session end (END) corresponding, respectively, to the beginning and the end of the recorded 24-hour profile, as well as a reference point indicating assuming a horizontal position for sleep (SLEEP) and a reference point indicating assuming a vertical position after sleep (WAKE);

identifying, for the recorded 24-hour profile of eyeball parameters, and with reference to the identified reference time points (START, SLEEP, WAKE, END), time points (TPI, TP2, TP3) such that at least the following subperiods are defined:

an initial subperiod (START—TP1) from session start to 5 hours before assuming a horizontal position for sleep;

a subperiod preceding assuming a horizontal position for sleep (TP1—SLEEP) from 5 hours before assuming a horizontal position to assuming a horizontal position for sleep;

a subperiod following assuming a horizontal position for sleep (SLEEP—TP2) from assuming a horizontal position for sleep to assuming a horizontal position for sleep+2 hours;

a subperiod preceding assuming a vertical position after sleep (TP2—WAKE) from assuming a horizontal position for sleep+2 hours to assuming a vertical position after sleep;

a subperiod following assuming a vertical position after sleep (WAKE—TP3) from assuming a vertical position after sleep to assuming a vertical position after sleep+2 hours;

a final subperiod (TP3—END) from assuming a vertical position after sleep+2 hours to the session end;

wherein the above division is chosen to reflect an individual variability of the 24-hour profile of the eyeball parameters and an influence of the cardiovascular and endocrine systems on this variability characteristic for a pathomechanism of glaucoma development and/or progression;

c) a step of reducing each of the measurement data series, for each one of the plurality of subjects, by transformations including determining, by the processor, in each subperiod, features describing a single subject in the form of at least one or more aggregating attributes, wherein the one or more aggregating attributes are selected from the group consisting of: a sum of the area under the curve in a subperiod, a slope angle of a linear regression line in a subperiod, a total variation in a subperiod, and representative values of the discrete Fourier transform in a subperiod; and calculating correlations between the eyeball parameters and the cardiovascular system parameters in the form of correlation parameters;

d) a step of creating, by the processor, a plurality of records each corresponding to one of the plurality of subjects, each record containing the one or more aggregating attributes and the calculated correlation parameters corresponding to a given subject;

e) a step of collecting a set of training records labelled for creating the predictive model for predicting glaucoma development and/or progression risk, wherein collecting the set of training records includes assigning, to each of the records created in step (d), using the processor, a label indicating a glaucoma diagnosis (glaucomatous neuropathy positive/negative) based on predetermined medical data for each of the plurality of subjects; and f) a step of creating, by the processor, the predictive model for predicting glaucoma development and/or progression risk, based on the set of training records created in step e) for the plurality of subjects, using supervised machine learning mechanisms based on one or more algorithms selected at least from regression algorithms, decision trees, Bayesian algorithms, ensemble algorithms and support vector-based algorithms, wherein the created predictive model reflects correlations between the eyeball parameters and the cardiovascular system parameters characteristic for a pathomechanism of glaucoma development in each defined subperiod used for training the predictive model;

wherein the set of training records are selected to control the creation of the predictive model by satisfying control parameters of sensitivity >0.85 and AUC >0.85 such that it provides high sensitivity to individual variability and an individual biorhythm of subjects, and embedding by the processor the predictive model for predicting glaucoma development and/or progression risk in the device memory;

the created predictive model receiving measurement data series for an individual subject to be examined, wherein said measurement data series are next processed as described in the steps b) to d) to produce an individual subject record containing a respective one or more aggregating attributes and correlation parameters of the record created in step d) and outputting a probability of said record to belong to a group of glaucomatous neuropathy development and/or progression risk positive or glaucomatous neuropathy development and/or progression risk negative subjects, wherein an output of the predictive model indicating glaucomatous neuropathy development and/or progression risk for the examined subject is generated by processing, using the predictive model, the individual subject record including correlations between eyeball parameters and cardiovascular parameters characteristic for a pathomechanism of glaucoma development and/or progression in each defined subperiod for the individual subject.

2. The method according to claim 1, wherein the predictive model for predicting glaucoma development and/or progression risk is created using 10-fold cross-validation.

3. The method according to claim 1, wherein one or more additional features selected from the group consisting of: subject's age, corneal resistance factor and corneal hysteresis are determined and appended to the record describing a single subject created in the step of the method.

4. The method according to claim 1, wherein the record describing a single subject in the step of the method is limited to a selected subset of the determined features.

5. The method according to claim 1, wherein the determined subperiods furthermore include a subperiod from the session start to assuming a horizontal position for sleep (START-SLEEP) and/or a subperiod from assuming a horizontal position for sleep to assuming a vertical position after sleep (SLEEP—WAKE) and/or a subperiod from assuming a horizontal position at 14:00 to assuming a vertical position at 15:30 with sustained consciousness (TIME 14:00-TIME 15:30).

6. A method for determining glaucoma development and/or progression risk in a subject, the method comprising:

creating, for a patient to be examined, a record containing the same feature set as the one created in the step of the method for creating a predictive model for predicting glaucoma development and/or progression risk, determining an allocation of the subject to a group of glaucomatous neuropathy development and/or progression risk positive or glaucomatous neuropathy development and/or progression risk negative subjects with determined probability using the predictive model for predicting glaucoma development and/or progression risk created according to the method of claim 1.

7. A system for predicting glaucoma development and/or progression risk in a subject using a predictive model for predicting glaucoma development and/or progression risk, comprising:

an eyeball parameters measuring and recording device configured to obtain eyeball parameters continuously or at intervals over a 24-hour period, wherein the eyeball parameters include a circumference at a corneoscleral limbus of an eyeball and/or an intraocular pressure;

a cardiovascular system parameters measuring and recording device configured to obtain cardiovascular system parameters continuously or at intervals over the 24-hour period, the cardiovascular system parameters including a systolic arterial pressure, a diastolic arterial pressure, a mean arterial pressure, and a heart rate;

a control circuit having a communication connection with the devices;

a processor installed in the control circuit;

a memory installed in the control circuit and operatively coupled to the processor;

an output device for presenting results having a communication connection with the control circuit;

wherein the processor is configured to execute a program code stored in the memory for performing the following steps based on a set of measurement data series provided by the devices, the set of measurement data series being for a plurality of subjects:

a step a of applying for each of the measurement data series a procedure of dividing the recorded 24-hour profile of the eyeball parameters, provided by the eyeball parameters measuring and recording device, wherein said procedure comprises:

identifying, for the recorded 24-hour profile of the eyeball parameters, reference time points including: session start (START) and session end (END) corresponding, respectively, to the beginning and the end of the recorded 24-hour profile, as well as a reference point indicating assuming a horizontal position for sleep (SLEEP) and a reference point indicating assuming a vertical position after sleep (WAKE);

identifying, for the recorded 24-hour profile of the eyeball parameters, and with reference to the identified reference time points (START, SLEEP, WAKE, END), time points (TPI, TP2, TP3) such that at least the following subperiods are defined:

an initial subperiod (START—TP) from session start to 5 hours before assuming a horizontal position for sleep;

a subperiod preceding assuming a horizontal position for sleep (TPI-SLEEP) from 5 hours before assuming a horizontal position to assuming a horizontal position for sleep;

a subperiod following assuming a horizontal position for sleep (SLEEP—TP2) from assuming a horizontal position for sleep to assuming a horizontal position for sleep+2 hours;

a subperiod preceding assuming a vertical position after sleep (TP2—WAKE) from assuming a horizontal position for sleep+2 hours to assuming a vertical position after sleep;

a subperiod following assuming a vertical position after sleep (WAKE—TP3) from assuming a vertical position after sleep to assuming a vertical position after sleep+2 hours;

a final subperiod (TP3—END) from assuming a vertical position after sleep+2 hours to the session end;

wherein the above division is chosen to reflect relationships between the eyeball parameters and the cardiovascular system parameters characteristic for a pathomechanism of glaucoma development;

a step b) of reducing each of the measurement data series, for each one of the plurality of subjects, by transformations including determining, in each subperiod, features describing a single subject in the form of one or more aggregating attributes, wherein the one or more aggregating attributes are selected from the group consisting of: a sum of the area under the curve in a subperiod, a slope angle of a linear regression line in a subperiod, a total variation in a subperiod, representative values of the discrete Fourier transform in a subperiod, and calculating correlations between the eyeball parameters and the cardiovascular system parameters, in the form of correlation parameters, provided by the cardiovascular system parameters measuring and recording device;

a step c) of creating a plurality of records each corresponding to one of the plurality of subjects, each record containing the one or more aggregating attributes and the calculated correlation parameters corresponding to said one of the plurality of subjects;

a step d) of collecting a set of training records, labelled for creating the predictive model for predicting glaucoma development and/or progression risk wherein collecting the set of training records includes assigning, to each of the created records in step c) using the processor, a label indicating a glaucoma diagnosis (glaucomatous neuropathy positive/negative) based on predetermined medical data for a respective subject of the plurality of subjects; and a step e) of creating the predictive model for predicting glaucoma development and/or progression risk, based on the set of training records created for the plurality of subjects, using supervised machine learning mechanisms based on one or more algorithms selected at least from regression algorithms, decision trees, Bayesian algorithms, ensemble algorithms and support vector-based algorithms, wherein the created predictive model reflects correlations between the eyeball parameters and the cardiovascular system parameters characteristic for a pathomechanism of glaucoma development in each defined subperiod used for training the predictive model;

wherein the set of training records are selected to control the creation of the predictive model by satisfying control parameters of sensitivity >0.85 and AUC >0.85 such that it provides high sensitivity to individual variability and an individual biorhythm of subjects, and embedding the predictive model for predicting glaucoma development and/or progression risk in the device memory;

wherein the processor is further configured to perform an additional step:

the created predictive model receiving measurement data series for an individual subject to be examined, wherein said measurement data series are next processed in the same way as described in the steps a) to c) to produce an individual subject record containing the one or more aggregating attributes and the calculated correlation parameters corresponding to said one of the plurality of subjects created in step c) and outputting a probability of said record to belong to a group of glaucomatous neuropathy development and/or progression risk positive or glaucomatous neuropathy development and/or progression risk negative subjects, wherein an output of the predictive model indicating glaucomatous neuropathy development and/or progression risk for the examined subject is generated by processing, using the predictive model, the individual subject record including correlations between the eyeball parameters and the cardiovascular system parameters characteristic for a pathomechanism of glaucoma development and/or progression in each defined subperiod for the individual subject.

8. The system according to claim 7, wherein the eyeball parameters measuring and recording device, the cardiovascular system parameters measuring and recording device and/or the output device are arranged in a remote location with respect to the control circuit, and the communication connections are communication network connections.

9. The method according to claim 2, wherein the aggregating attributes are selected from the group consisting of: a sum of the area under the curve in a subperiod, a slope angle of a linear regression line in a subperiod, a total variation m a subperiod, representative values of the discrete Fourier transform in a subperiod.

10. The method according to claim 2, wherein the eyeball parameters are selected from the group consisting of: a circumference at a corneoscleral limbus of an eyeball and intraocular pressure.

11. A system for predicting glaucoma development and/or progression risk in a subject according to a system for predicting glaucoma development and/or progression risk in a subject according to claim 7, wherein the processor is furthermore configured to execute the program code stored in the memory for performing the following steps creating, for a patient to be examined, an individual subject record containing a feature set including the correlation parameters of the record created by the processor performing the step, determining an allocation of the subject to a group of glaucomatous neuropathy development and/or progression risk positive or glaucomatous neuropathy development and/or progression risk negative subjects with determined probability using the predictive model for predicting glaucoma development and/or progression risk embedded in the memory and sending the same to the output device.

12. The method of claim 1, wherein the eyeball parameters measurement and recording device includes a continuous ocular monitor, the continuous ocular monitor including a sensor in a contact lens.

13. The method of claim 1, wherein the cardiovascular system parameters measuring and recording device includes a continuous cuffless blood pressure monitor.

14. The system of claim 7, wherein the eyeball parameters measurement and recording device includes a continuous ocular monitor, the continuous ocular monitor including a sensor in a contact lens.

15. The system of claim 7, wherein the cardiovascular system parameters measuring and recording device includes a continuous cuffless blood pressure monitor.

16. The method of claim 1, further comprising providing local or systemic therapy to the individual subject based on the output of the predictive model indicating glaucomatous neuropathy development and/or progression risk.

* * * * *